United States Patent [19]

Fischell et al.

[11] Patent Number: 4,886,061
[45] Date of Patent: Dec. 12, 1989

[54] EXPANDABLE PULLBACK ATHERECTOMY CATHETER SYSTEM

[75] Inventors: Robert E. Fischell, Dayton, Md.; Tim A. Fischell, Los Altos, Calif.

[73] Assignee: MedInnovations, Inc., Dayton, Md.

[21] Appl. No.: 153,912

[22] Filed: Feb. 9, 1988

[51] Int. Cl.⁴ .............................................. A61B 17/32
[52] U.S. Cl. .................................... 128/305; 128/304; 604/22
[58] Field of Search ............... 128/304, 305, 751, 754, 128/755; 604/22, 105, 108, 267

[56] References Cited

U.S. PATENT DOCUMENTS

| | | | |
|---|---|---|---|
| 1,167,014 | 1/1916 | O'Brien | 128/305 |
| 2,505,358 | 4/1950 | Gusberg et al. | 128/305 |
| 2,541,691 | 2/1951 | Eicher | 128/304 |
| 2,730,101 | 1/1956 | Hoffman . | |
| 3,472,230 | 10/1969 | Fogarty | 128/304 |
| 4,207,874 | 6/1980 | Choy . | |
| 4,273,128 | 6/1981 | Lary . | |
| 4,696,667 | 9/1987 | Masch | 128/304 |
| 4,765,332 | 8/1988 | Fischell et al. | 128/304 |

FOREIGN PATENT DOCUMENTS 0764684  9/1930  U.S.S.R. ............................. 128/325

Primary Examiner—Stephen C. Pellegrino
Assistant Examiner—Ralph Lewis

[57] ABSTRACT

Disclosed is an Expandable Pullback Atherectomy Catheter (EPAC) comprising a distal tip portion capable of assuming two diameters. The distal tip portion includes an expandable cutting means and an expandable tissue collecting means. The catheter is guided in an artery to the stenosis and the distal tip is urged past the stenosis while being maintained in a compressed state by a sheathing catheter. The sheathing catheter is withdrawn allowing the cutting means and collecting means to expand. The stenotic tissue is removed by pulling the distal tip back in a retrograde direction while the cut tissue is captured in the collecting means. Additional structural details are provided to prevent injury to the inner wall of an artery and to avoid total obstruction of the artery during the antherectomy procedure.

38 Claims, 4 Drawing Sheets

U.S. Patent    Dec. 12, 1989    Sheet 1 of 4    4,886,061
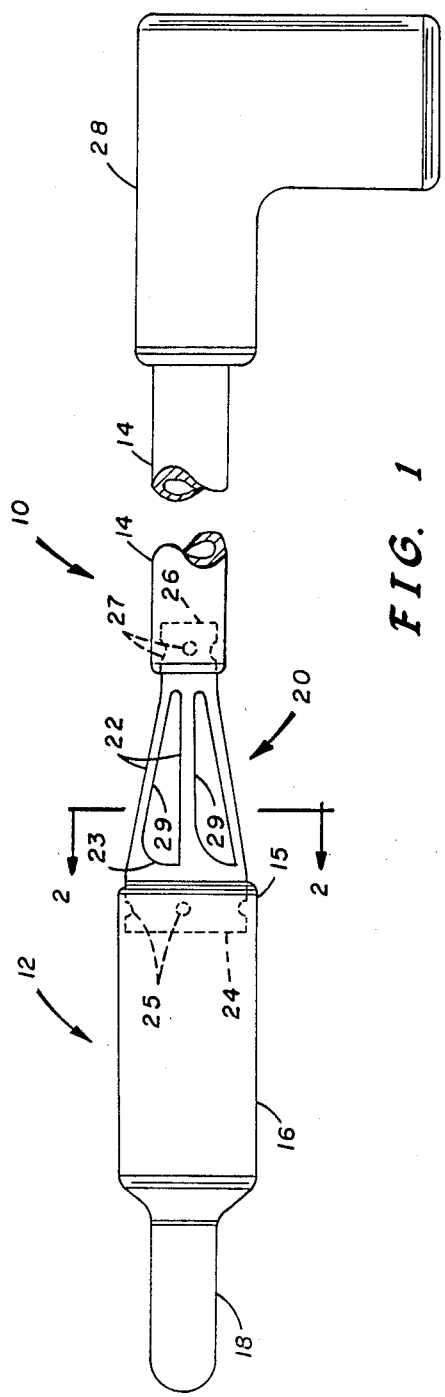
FIG. 1
FIG. 2
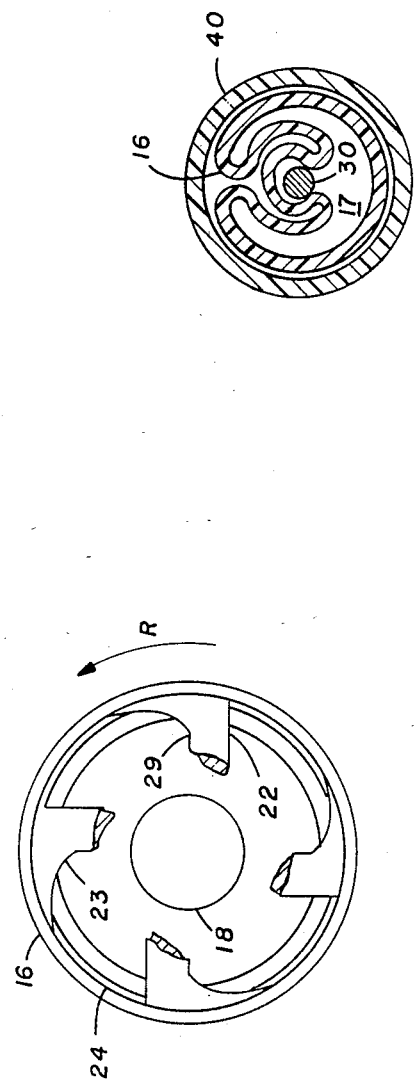
FIG. 5

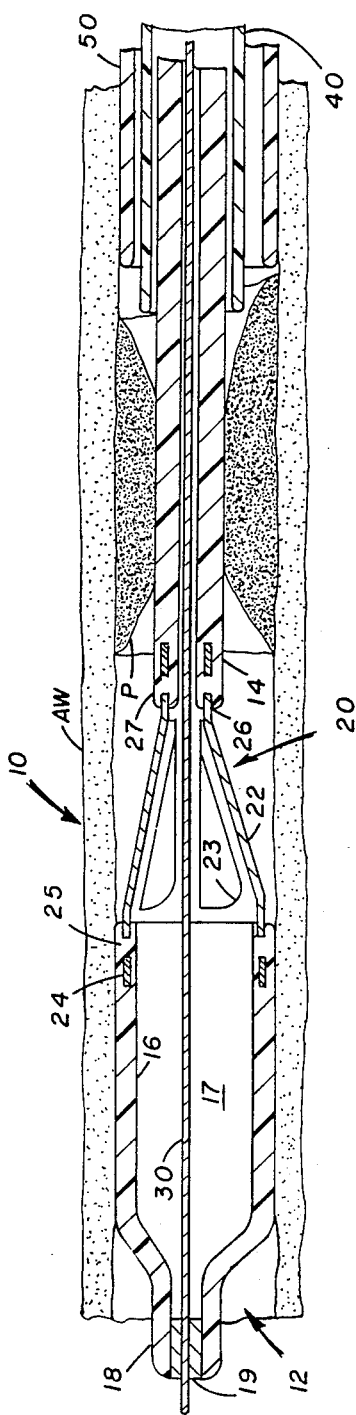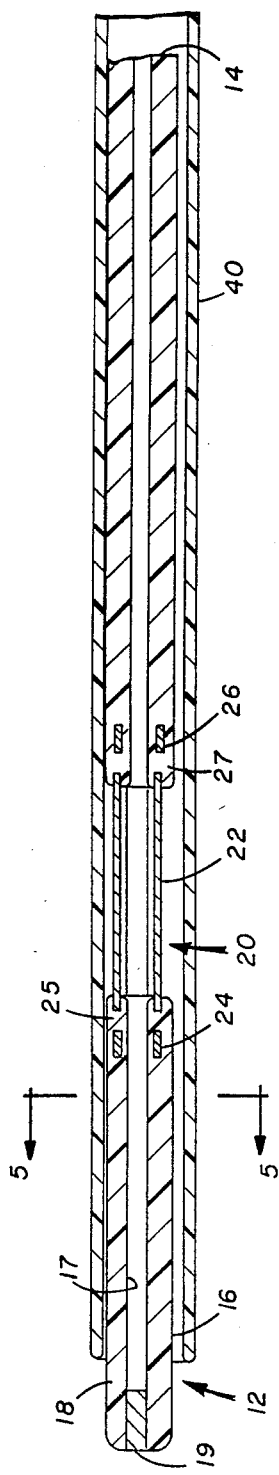

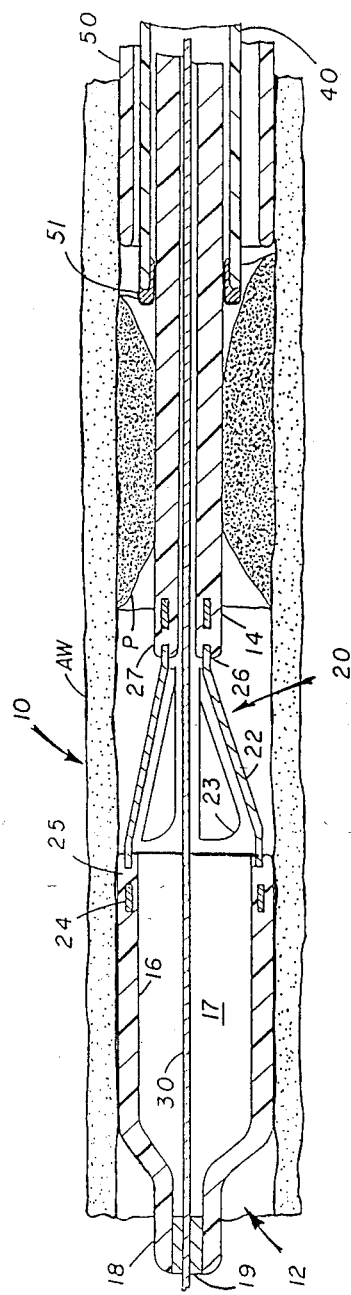

EXPANDABLE PULLBACK ATHERECTOMY CATHETER SYSTEM

FIELD OF THE INVENTION

This invention is in the field of intraoperative and percutaneous transluminal arterial catheters designed for surgical excision of atheromas which typically consist of plaque deposits that cause narrowing (stenosis) of an artery. The cutting out of atheromas has been given the name "atherectomy".

BACKGROUND OF THE INVENTION

Atherosclerotic arterial disease is the leading cause of morbidity and mortality in the United States and most other developed countries. Atherosclerosis is a chronic disease process characterized by lipid deposits and fibrosis of the intima, irregularly distributed in large and medium sized arteries. The disease is progressive and most often becomes clinically manifested in the middle-aged and elderly. When severe, the atherosclerotic plaque causes a reduction of the cross-sectional area of the arterial lumen, with and without thrombosis. Resultant ischemic manifestations include angina pectoris, myocardial infarction, stroke, intermittent claudication, gangrene of the lower extremities and renovascular hypertension.

The current management of atherosclerotic disease includes preventative therapy aimed at minimizing known major risk factors such as hypertension, smoking, hypercholesterolemia and diabetes mellitus.

Coronary artery bypass grafting (CABG), carotid endarterectomy and bypass grafting (autogenous vein or synthetic graft) of the iliac, femoral and renal arteries are all well established surgical methods of palliative therapy. Although these procedures are often effective in relieving ischemia, each of these represents a major surgical operation with significant associated morbidity, mortality and expense. CABG, for example, requires the opening of the chest cavity (thoracotomy) and use of cardiopulmonary bypass, with not uncommon post-operative complications including postpericardotomy syndrome, Non-A Non-B hepatitis, stroke and a mortality of approximately one percent (1%)

Percutaneous transluminal angioplasty (PTA) by means of a balloon catheter is a relatively new "non-surgical" procedure with proven efficacy in relief of atherosclerotic obstruction of the coronary, renal and peripheral circulations. The technique involves the percutaneous passage (under local anesthesia) of a specialized balloon tipped catheter through the site of arterial narrowing, and inflation of the balloon to reduce obstruction. This is always done in conjunction with angiographic visualization of the vessel being treated. When successful, this procedure results in a reduction of the arterial stenosis and a decrease in the transstenotic pressure gradient. The mechanism of action is felt to consist of some combination of plaque compression, intimal splitting and medial/adventitial stretching. Healing of the balloon-damaged plaque may involve fibrosis and retraction of the split intimal elements, with further luminal enlargement in the weeks to months following the procedure.

The safety and efficacy of PTA is a function of the vessel being treated, patient selection, and the expertise of the physician performing the procedure. Primary angiographic success, defined as a 20% or greater reduction of stenosis, is now achieved in approximately 80-90% of attempts in carefully selected patients at experienced centers. The obvious advantage of PTA, compared to surgical palliative therapy, is that it does not require major surgery or general anesthesia with the associated sequelae.

Despite its proven efficacy in the palliation of obstructive atherosclerotic disease, PTA, as it is currently performed, has several important technical limitations. These limitations are particularly true in the application of PTA to the coronary circulation.

Even in the most skilled hands, dilation of an arterial obstruction is currently not achievable in approximately 20% of attempts. The most common cause of failed PTA is the inability to pass either the guidewire or dilating catheter through the site of a tight or eccentric stenosis. This problem is even more common in attempts to dilate the difficult to access right and circumflex coronary arteries. Although technical advances, such as steerable catheters, have reduced the frequency of unsuccessful attempts, inability to cross tight, eccentric or fully closed stenosis remains a major limitation of PTA.

Attempts at balloon or guidewire passage in vessels which are tightly stenotic may lead to arterial dissection and/or acute occlusion necessitating emergency vascular surgery. This major complication occurs in 6-8% of attempts at coronary angioplasty.

Inability to dilate an obstruction, even after proper balloon positioning and inflation is a second common mode of PTA failure. This problem is most frequently encountered in older plaques which are densely fibrotic and/or calcified.

Restenosis of the obstructed arterial segment following successful PTA is major problem with the current technique. This problem is more common following PTA of a coronary obstruction (30-35% at one year) than in the peripheral circulation (10-15% at two years). Pharmacologic attempts to reduce the incidence of restenosis have been largely unsuccessful.

Distal embolization of atherosclerotic plaque following balloon PTA occurs in approximately 5% of patients undergoing PTA of lower extremity or renal arteries. Although emboli are usually clinically insignificant in these vascular territories, such embolization could be catastrophic in the cerebral circulation. For this reason, balloon PTA is considered to be contraindicated for the treatment of obstructive lesions in the arteries of the aortic arch, such as the carotid artery.

DESCRIPTION OF THE PRIOR ART

In U.S. Pat. No. 4,207,874 (dated June 17, 1980) D. S. J. Choy describes a means for using a laser beam to tunnel though an arterial occlusion by vaporization of the obstruction. The difficulty with Choy's technique is that there is insufficient means to prevent simultaneous destruction of the arterial wall. For example, the Choy invention shows an intense laser beam aimed in the forward direction without significant beam attenuation. If the artery were to curve and the arterial wall were to be exposed to the laser beam, the wall could also be vaporized which could be catastrophic for the patient. Although the Choy patent describes a means for direct visualization of the obstructed region, it does not describe a centering means or a guidewire following means in order to guarantee that the laser beam does not illuminate part of the arterial wall. Furthermore, the Choy device may completely block a partially obstructed artery thereby cutting off blood flow to distal tissues for a significant time period. The result is ischemia which could cause irreparable damage to heart or brain tissue. Furthermore, if laser oblation was used in the carotid arteries, resulting gas bubble formation could cause some cerebral ischemia and resulting permanent brain damage.

In U.S. Pat. No. 4,273,128 (dated June 16, 1981) B. G. Lary describes a coronary cutting and dilating instrument used for opening a coronary stenosis that is restricting blood flow. The device described by Lary could not be used in a completely or nearly completely occluded artery because of its "blunt ovoid tip" nor could it pass through a very narrow stenosis. Furthermore, the Lary concept does not have any means to prevent its cutting blade from cutting through the arterial wall. Furthermore, there is no means taught in the Lary patent for centering the cutting blade within the arterial walls. Thus, if the probe wire 13 (FIG. 10) of the Lary patent guides the knife through a highly eccentric lumen within the stenotic plaque, its knife blade could cut through the arterial wall resulting in serious adverse effects for the patient.

Similar to the Lary device (although actually in a different field of use, namely removing growths from the teats of cows) is the device disclosed in U.S. Pat. 2,730,101 (dated Jan. 10, 1956) by R. D. Hoffman and entitled "Teat Bistoury with Expandable Cutter Knives." FIGS. 1, 2 and 3 of the Hoffman patent show an expansible cutter knife which can be inserted closed, opened within the teat, rotated to allow cutting of teat obstructions and then closed to withdraw the device from the canal. The Hoffman device has no means for preventing the blades from cutting the vessel wall, and hence if used within a human artery, such a rotating or oscillating blade would cut through the arterial wall. Because the flow of milk is out of the cow's body, particulate matter released during cutting with the Hoffman device would not harm the animal; however, in the entirely different field of use in the artery of a human, the absence of a definitive plaque collection means in the Hoffman device would result in the release of particulate matter into the flowing blood. Such particulate matter could then flow distally causing ischemia, stroke or even death. Thus the Hoffman device is entirely unsuitable for use in human (or animal) arteries.

Further advances are described in prior patent application Ser. Nos. 874,140 filed on June 13, 1986, and 694,746 filed on Jan. 25, 1985, both by Robert E. and Tim A. Fischell entitled "A Guide Wire Following Tunneling Catheter System for Transluminal Arterial Angioplasty", and "A Tunneling Catheter System for Transluminal Arteral Angioplasty", respectively. The '140 application describes a deice for removing stenotic plaque by advancing a tunneling catheter over a guidewire and within a guiding catheter. In this prior invention, the cutting is done by advancing the cutting catheter in a forward (antegrade) direction. The '746 application which is incorporated herein by reference, describes the use of a centering catheter which has expandable spokes to engage the inner arterial wall for centering the catheter. Plaque is removed by advancing a similar tunnelling catheter described in the '140 application. A potential difficulty in such a procedure is the inability to exert enough forward force to cut through a hard calcified plaque. Furthermore, if the tunneling catheter is advanced too far in the forward direction, it could cut the arterial wall. Even with the use of cutting (as opposed to fracturing the plaque which occurs with balloon dilation) there would still be the possibility of some particulate matter flowing into the bloodstream which could result in some distal ischemia.

Another application, Ser. No. 885,139 filed on July 14, 1986 by Robert E. and Tim A. Fischell and entitled "A Pullback Atherectomy Catheter System," describes the concept of first penetrating the stenotic plaque in a forward direction with a hollow conically pointed metal tip and then pulling the tip back in a retrograde direction. The tip, which includes a cylindrical cutting edge, is designed to shave off a cylindrical layer of the plaque as it is pulled back in the retrograde direction. Thus, the force required to perform the cutting is exerted by pulling back on the catheter (a retrograde motion) as opposed to cutting with a forward (antegrade) motion. The PAC utilizes sequentially larger diameter tips which progressively enlarge the lumen of the stenotic plaque.

PAC devices would typically be guided to the stenosis by a guidewire that is first passed through the narrowed lumen. Each one of the sequentially larger PAC tips is first advanced within a guiding catheter and over a guidewire until the tip passes through the stenotic plaque. The PAC tip is then pulled back to shave off plaque; then the PAC is withdrawn from the body. Each tip includes a chamber designed to collect the shaved off plaque thus preventing plaque particles from entering the bloodstream. Although PAC offers considerable advantage over prior atherectomy systems, it has three distinct disadvantages. Specifically, (1) the plaque collection chamber in the tip is both rigid and reasonably long which makes it difficult to use in highly curved arteries, (2) the tip diameter is limited to that diameter (approximately 3 mm) which could be readily inserted through a percutaneous guiding catheter passing through the femoral artery at the location of the patient's groin, and (3) to the extent that the plaque is not elastic, the cylindrical hole made in the plaque by the PAC tip moving in a forward (antegrade) direction precludes the removal of plaque when the tip is moved in the retrograde direction because the tip keeps the same diameter when moving in each of these two directions.

SUMMARY OF THE INVENTION

It is the goal of the present invention to eliminate the numerous shortcomings of the prior art in order to provide an extremely flexible and expandable device which can safely tunnel a clean hole through virtually any arterial stenosis without cutting the arterial wall or creating gas bubbles, or causing the release of particulate matter into the bloodstream.

The Expandable Pullback Atherectomy Catheter (EPAC) described herein operates by first passing the EPAC through a guiding catheter that has been intraoperatively or percutaneously inserted within an artery and then penetrating the stenotic opening in a forward direction with the tip diameter small enough to pass through the stenosis. When inserted into the artery, the EPAC tip is compressed by means of a sheathing catheter that completely encloses its tip. Once past the arterial stenosis, the sheathing catheter, which fits inside the guiding catheter, is pulled back thus allowing the EPAC tip diameter to radially expand to its full size. The expanded EPAC tip is then pulled back through the stenotic plaque with a retrograde motion while spinning which cuts through the plaque and causes the plaque particles to be collected in a flexible plaque collection chamber. The EPAC with the captured plaque is then pulled back through the guiding catheter and completely out of the body. The process is then repeated with sequentially larger expanded diameters of the EPAC tips until the lumen of the artery is sufficiently enlarged to allow adequate blood flow.

As described in prior application Serial No. 874,140 noted above, the cutting action of the EPAC tip is enhanced by rotation, or by applying high energy ultrasonic vibration to the cutting edges or possibly by the application of an electrocautery current applied at the cutting edges. These means for cutting enhancement would be applied only during pullback.

Thus an object of the present invention is to safely remove stenotic plaque material by first advancing a small diameter EPAC tip through the stenotic lumen, then allowing that tip to expand its diametric size, and then shaving off stenotic plaque by pulling the rotating cutting edges of the tip back through the stenosis in a retrograde direction.

Another object of the present invention is to collect the shaved off plaque in a flexible collection chamber within the tip and then remove the entire EPAC including the collected plaque from the body.

Still another object of the present invention is to reduce the thrombogenicity of the plaque collection chamber by heparinizing the walls thereof.

A further object of the present invention is to provide a plaque collection chamber which is sufficiently porous to allow blood to flow therethrough while still collecting all shaved plaque which could result in distal embolization.

Still another object of the present invention is to reduce the diameter of the EPAC tip after cutting through the stenosis so that the EPAC can be removed through a comparatively small diameter guiding catheter.

Still another object of the present invention is to utilize ultrasonic vibration of the cutting edges to facilitate the ability of the device to cut through the plaque.

Still another object of the present invention is to utilize an electrocautery electric current at the cutting edges of the EPAC tip to enhance the ability of the device to cut through the plaque.

Still another object of the present invention is to use sequentially larger diameter tips each sequentially pulled back through the stenotic plaque to progressively enlarge the lumen of the stenosis.

Still another object of the present invention is to first use the EPAC to bore a tunnel into the plaque and then use balloon angioplasty to further enlarge the lumen of the stenotic plaque.

Still another object of the present invention is to first use balloon angioplasty to enlarge a very narrow stenotic lumen and then to use the EPAC to further enlarge the arterial lumen by excising the plaque.

Still another object of the present invention is to first use a heated tip catheter or a laser beam to open a fully occluded artery and then to use the EPAC to further enlarge the arterial lumen by excising the remaining plaque.

Still another object of the present invention is to use the EPAC system to remove plaque deposited at a branch point of an artery, i.e., to open an ostial stenosis.

Still another object of the present invention is to use the EPAC to remove thrombotic tissue from an artery or to simultaneously remove thrombotic tissue and plaque.

Still another object of the present invention is to remove any obstructive tissue from artificial vessel grafts or from bypass veins.

Still another object of the present invention is to apply a coating to the EPAC that improves lubricity.

Still another object of the present invention is to apply the EPAC system for opening of any stenotic or occluded artery including the coronary arteries, the carotid artery, the renal, iliac or hepatic arteries and the arteries of the arms and legs or bypass veins or vessel grafts.

BRIEF DESCRIPTION OF THE DRAWINGS

FIG. 1 illustrates the Expandable Pullback Atherectomy Catheter (EPAC) attached to a spinning means with the tip in its expanded state.

FIG. 2 is an enlarged, cross-sectional view through line 2-2 in FIG. 1 of the cutting blades of the Expandable Pullback Atherectomy Catheter.

FIG. 3 is a cross-sectional view of an artery showing the Expandable Pullback Atherectomy Catheter system with its tip located just distally from a stenotic plaque or atheroma and with the tip in its expanded state.

FIG. 4 is a cross-sectional view of the Expandable Pullback Atherectomy Catheter and sheathing catheter with the EPAC tip in its compressed state.

FIG. 5 is an enlarged cross-sectional view through line 5-5 in FIG. 4 of the EPAC tip in its compressed state showing the guidewire and sheathing catheter and also showing the plaque collection chamber in its compressed state.

FIG. 7 is an enlarged cross-sectional view of the Expandable Pullback Atherectomy Catheter of FIG. 3 showing an alternate embodiment of the sheathing catheter.

DETAILED DESCRIPTION OF THE INVENTION

Figure 6:
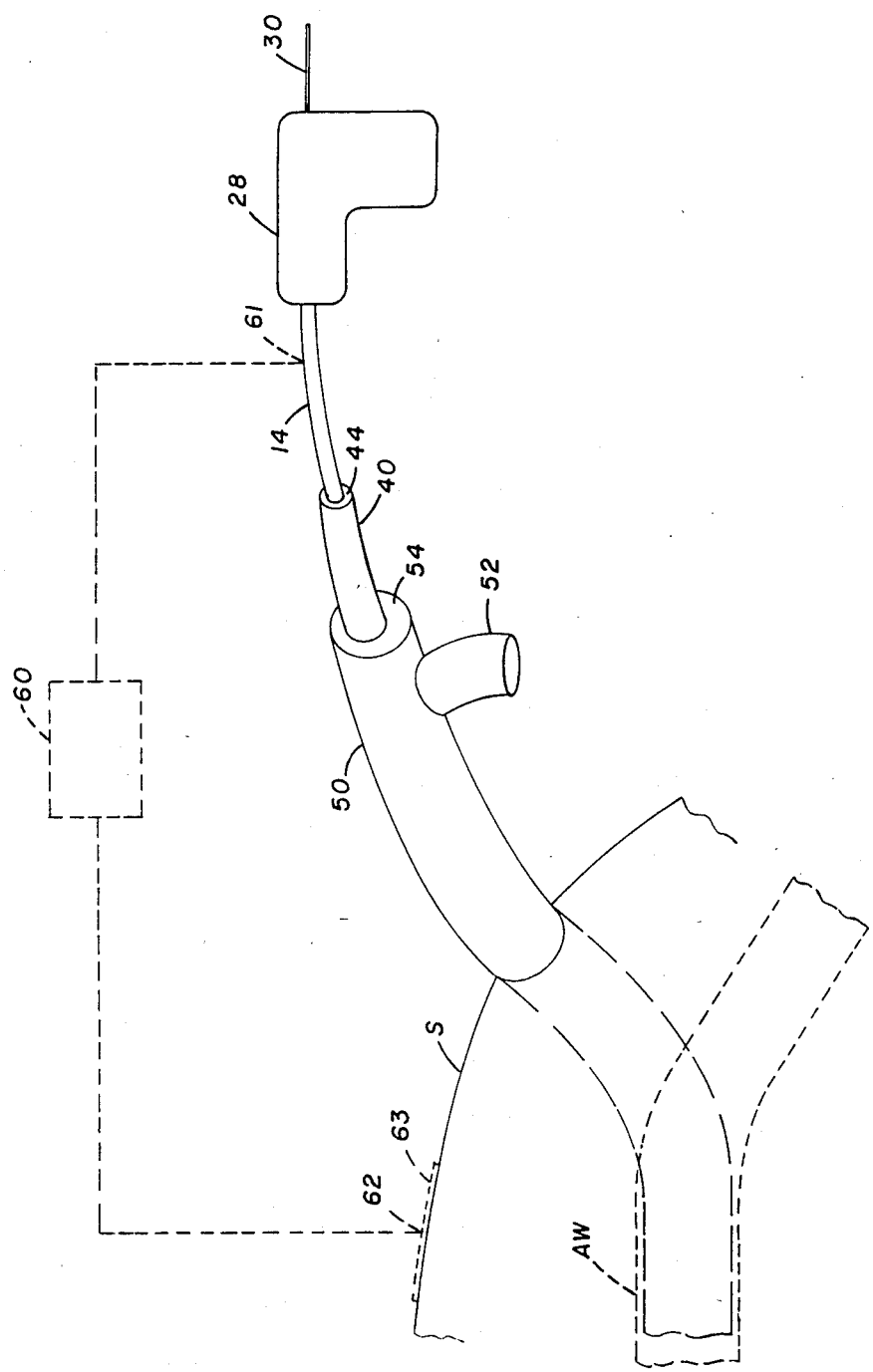
FIG. 6 shows the arrangement of the proximal portion of the Expandable Pullback Atherectomy Catheter system as it is configured external to the patient's body.

FIG. 1 illustrates the Expandable Pullback Atherectomy Catheter (EPAC) 10. FIG. 2 is an enlarged cross-sectional view of the EPAC 10 at 2—2 of FIG. 1. The other parts of the EPAC system (all shown in FIG. 3) are the guidewire 30, the sheathing catheter 40, and the guiding catheter 50.

Referring first to FIG. 1, the principal parts of the EPAC 10 are a distal tip 12, a radially expandable conical cutter 20, a torquing catheter 14, and a rotating means 28. The distal tip 12 consists of a small diameter distal portion 18 and a radially expandable plaque collection chamber 17 (FIG. 3) defined by the wall 16. The conical cutter 20 consists of a multiplicity of cutter blades 22 that are attached at their distal ends to distal ring 24 and at their proximal ends to the proximal ring 26. The distal ring 24 is radially expandable and is molded into the plaque collection chamber wall 16. Distal ring 24 takes the same cross-sectional shape as the collection chamber 16 when expanded or compressed. The proximal ring 26 (which is not expandable) is molded into the torqueing catheter 14. Attachment holes 25 in the proximal ring 26 assist in maintaining a strong connection with the wall 16 into which the ring is molded. The proximal ring 26 has attachment holes 27 which enhance the strength of the connection when the ring 26 is molded into the torqueing catheter 14.

The shoulder 15 which lies over the distal ring 24 prevents the distal ring 24 and hence the conical cutter 20 from coming in contact with the arterial wall. Thus, distal ring 24 and its shoulder 15 act as centering devices to protect the inner arterial walls from being cut by blades 22. Ring 24 also compensates for unequal plaque build-up along the arterial walls by deforming appropriately as the device passes through the stenosis. The torqueing catheter 14 is attached at its proximal end to a spinning means 28 which is typically a drill designed for use in an operating room; such a device could be the System II Drill, Catalogue No. 298-92 of Stryker Surgical Co., Kalamazoo, Mich.

When the EPAC 10 is pulled back through stenotic plaque while the cutter 20 is simultaneously rotated by the spinning means 28 in a counterclockwise direction (as seen from the proximal direction) then, as seen in FIGS. 1 and 2, the longitudinal sharpened edges 29 of the blades 22 cut through the plaque and force the plaque into the collection chamber 17. The direction arrow R of FIG. 2 indicates the rotational direction of the EPAC tip. A curved sharpened edge 23 of each blade 22 enhances the cutting action by providing a slicing motion through the plaque as the EPAC is rotated while being pulled back in a retrograde direction.

The conical cutter 20 which includes the distal ring 24 and the proximal ring 26 is typically made from a hard spring steel, or from another spring material such as berylium copper. The metal thickness is typically between 2 and 10 mils. The plaque collection chamber wall 16 is typically between 5 and 20 mils thick, and of a flexible plastic such as MYLAR (polyester), TEFLON (polytetrafluoroethylene or Nylon. Ideally the wall 16 would be made porous with pore size between 20 and 50 microns so that blood plasma, red and white cells and platelets could pass through, thus allowing perfusion of distal tissue to minimize risk of damaging heart tissue or brain cells caused by lack of blood. Plaque of this small size could also pass through with no harm to the patient. The distal ring 24 and the plaque collection chamber is typically made in various sizes with diameters (when expanded) from as small as 2 mm to as large as 10 mm with total chamber length from 0.5 to 10 cm. The proximal ring 26 and torqueing catheter 14 is typically made in various sizes with diameters ranging from 1 mm to 4 mm. The torqueing catheter 14 would typically be made from a stiff, strong plastic such as PVC with a wall thickness between 10 and 20 mils.

Although the cutter blades 22 are shown as being essentially straight from their smaller diameter at the proximal ring 26 to their larger diameter at the distal ring 24, they could have a variety of shapes, positions, angles and number of blades in order to enhance their cutting action.

FIG. 3 is a cross-sectional view of the entire EPAC system which includes the EPAC 10, the guidewire 30, the sheathing catheter 40 and the guiding catheter 50 all shown within an artery having an atheromatous plaque P within the arterial wall AW. In FIG. 3 the sheathing catheter 40 is shown pulled back so that the distal tip 12 and the conical cutter 20 have expanded radially to their full diameter. With the aid of angiography, after the tip 12 has been advanced beyond the stenosis, the EPAC tip 12 is pulled back while spinning until a cylindrical tunnel has been bored through the plaque. The plaque is collected in the plaque collection chamber 17 and then the rotation is stopped. The EPAC 10 and the sheathing catheter 40 are then pulled back through the guiding catheter 50 until they are totally removed from the patient's body. A packing gland 19 typically of sponge rubber is placed to completely prevent plaque from escaping from the plaque collection chamber 17 while the guidewire 30 remains in place and the EPAC 10 is withdrawn from the patient's artery. However, a clearance of 20 to 50 microns between the outside diameter of the guidewire 30 and the packing gland 19, would allow acceptably small particulate matter to escape from the plaque collection chamber 17 as well as allowing the flow of some blood which is desirable.

The procedure described above could be repeated if necessary with an EPAC tip 12 that has a larger expanded diameter. This procedure can be repeated with successively larger diameter tips 12 until the stenotic lumen is sufficiently enlarged to allow adequate blood flow.

When the EPAC tip 12 is rotated by means of applying torque to the torqueing catheter 14 by means of the spinning means 28 (all shown in FIG. 1), the guidewire 30 could be allowed to spin or could remain fixed. Furthermore, the sheathing catheter 40 might be allowed to spin or it might remain non-rotating. However, the guiding catheter 50 preferably would remain fixed (i.e., non-rotating relative to the arterial wall AW). Further, it may be advantageous to spin the conical cutter 20 while slidably connecting the plaque collection chamber 17 so that the chamber 17 does not spin.

The risk of cutting the arterial wall is highest when the conical cutter is expanded. As shown in FIG. 3, the thickness (typically 2 to 20 mils) of the plastic material of the shoulder 15 of the plaque collection chamber 17, prevents even the largest diameter portion of the conical cutter 20 from cutting into the arterial wall.

Although the collection chamber 17 is shown in FIG. 3 to be essentially cylindrical in shape, it might also be conical in shape with its large mouth opening proximally. Chamber 17 also could have a much longer, smaller diameter distal portion 18, with only a very short proximal section of a diameter large enough to cover the distal ring 24. Designs having a smaller diameter of the plaque collection chamber 17 as compared to the distal ring 24, would decrease the contact of the wall 16 with the delicate intimal lining of the arterial wall AW. This could minimize damage to the intima during insertion, spinning and removal of the EPAC 10.

Although the spinning mode has been discussed extensively herein, the use of ultrasonic vibration or electrocautery cutting during pullback with or without rotation would be another practical means for accomplishing atherectomy. For example, if the torqueing catheter 14 were fabricated from a thin wall metal tube, such a tube could be used to transmit ultrasonic vibration to the cutting edges 23 and 29 during pullback thus accomplishing the desired atherectomy. In this case, an ultrasonic vibration generator would replace the spinning means 28.

Yet another technique would be to use a metal tube torqueing catheter 14 that is insulated on all its surfaces except at its proximal end, which is external to the body. In this technique the conical cutter 20 would be electrically connected to the torqueing catheter 14 and would also have electrical insulation throughout all its surfaces except at the cutting edges 23 and 29. One terminal of a conventional electrocautery current generator would be connected to the conducting proximal end of the torqueing catheter 14, with the ground connection of the generator being connected to the patient's skin. As the assembly 10 is pulled back, the electrocautery current emanating from the sharp edges 23 and 29 would assist in performing the desired atherectomy. Cutting with this technique is analogous to cutting with an electrocautery scalpel as regularly used in surgical procedures. Such an electrocautery atherectomy would have the additional advantage of cauterizing the cut interior surface of the arterial wall thus reducing its tendency to form thrombi.

FIG. 4 shows the sheathing catheter 40 extended over and therefore compressing the distal tip 12 of the EPAC 10. Although the proximal ring 26 retains its precompression size, the distal ring 24 follows the plaque collection chamber wall 16 when deformed as shown so as to fit within the sheathing catheter 40. The distal tip 18 and the packing gland 19 of the plaque collection chamber 17 are not compressed by the sheathing catheter 40.

When the EPAC 10 is pushed through the stenotic lumen, the sheathing catheter 40 might be pushed through first, or alternatively the EPAC 10 could be inserted until the sheathing catheter 40 just stops proximally against the stenosis; then the tip 12 would be pushed through. This latter method minimizes the diameter of that which must be pushed through the stenotic lumen. The smaller diameter distal tip 18 of the plaque collection chamber 17 is designed for and serves to assist in passing the distal tip 12 through a tight stenosis with the sheathing catheter 40 stopping just proximal to that stenosis.

When the distal tip 12 is pulled back through the stenotic plaque P (FIG. 3), the sheathing catheter 40 can be pushed over the distal tip 12 to compress the tip 12. Alternatively, the guiding catheter 50 can be used to compress the tip 12. Using the guiding catheter 50 for this purpose during pullback would allow the greatest volume of the compressed plaque to be held within the collection chamber 17; this would be necessary if a large volume of plaque was collected. If such a large volume of plaque was collected that even the guiding catheter 50 was incapable of containing the plaque filled chamber 17, then the proximal end of the distal ring 24 would be pulled back until it touched the mouth of the guiding catheter 50, and then the entire EPAC system including the guiding catheter 50 would be removed from the patient's body.

The walls 16 of the plaque collection chamber 17 in both FIGS. 3 and 4 have an exaggerated thickness in order to better show the details of connection to the distal ring 24. In the preferred embodiment, the walls 16 are 10 mils thick and would be made from a tough yet flexible (and possibly porous) plastic such as MYLAR (polyester, TEFLON (polytetrafluoroethylene or Nylon. Thus the collection chamber 17 could be many centimeters long and still easily bend around highly curved arteries such as some of the coronary arteries. Furthermore, as shown in FIG. 5, an appropriately thin wall 16 takes up less volume when the tip 12 is in its compressed state. Additionally, the collecting chamber 17 could be coated with heparin in order to reduce thrombus formation.

FIG. 6 illustrates the proximal configuration of the EPAC system external to the patient's body. The guiding catheter 50 is shown penetrating the patient's skin S and entering within the arterial wall AW. A side port 52 on the guiding catheter 50 can be used to inject flushing (saline) solution or angiographic dye, or to apply a suction at the distal end of the guiding catheter 50.

Emerging from a packing gland 54 at the proximal end of the guiding catheter 50 is the sheathing catheter 40, and emerging from a packing gland 44 at the proximal end of the sheathing catheter 40 is the torqueing catheter 14 which is attached to a rotating means 28. The guidewire 30 passes through a packing gland at the proximal end of the torqueing catheter 14 and it then passes through a cannula within the spinning means 28. The guidewire 30 would be made long enough so that the entire EPAC system (except for the guiding catheter 50) could be removed from the body while the guidewire 30 remains in place through the stenotic lumen.

If ultrasonic vibration is used, the spinning means 28 of FIG. 6 would be replaced with a conventional generator of ultrasonic (or even sonic) vibrations. If electrocautery is used, the connections would be as shown by dotted lines in FIG. 6; that is, a conventional electrocautery current generator 60 would have one terminal 61 attached to the non-insulated proximal end of a metal torqueing catheter and its ground terminal 62 attached to a grounding plate 63 in contact with the patient's skin "S".

Although the removal of plaque from a human artery has been described in detail herein, the EPAC 10 can be advantageously used for safely removing many types of obstructions from any vessel within a human or animal. For example, blood flow obstructions occurring in arterial blood vessel grafts or bypass veins are particularly well suited for removal by the EPAC. Furthermore, thrombi and plaque could be separately or simultaneously removed from blood vessels thus enlarging such lumens to provide adequate blood flow. Finally, the EPAC could be used for opening of other lumen ducts such as urethra, ureter, bile ducts or fallopian tubes. In all cases, the EPAC provides means for removing obstructive tissue from a vessel in a living body in lieu of balloon angioplasty which merely redistributes such material.

The utility of the EPAC to open arteries can also be enhanced by the adjunctive use of conventional balloon angioplasty. For example, a narrow stenosis might first be enlarged from less than 1 mm to 2 mm or greater, and then the EPAC could be used to remove the deformed plaque. Furthermore, the use of a heated tip catheter or a laser beam to first open a small lumen in a fully occluded artery, followed by the use of the EPAC for plaque removal offers a unique and valuable therapy for obtaining long term patency of even fully occluded arteries.

Furthermore, the EPAC system can be used with a separate means for plaque removal, such as plaque removal by cutting, grinding or by the use of lasers, performed proximal to the EPAC distal plaque collection chamber 17. The chamber 17 would then be used for the sole purpose of collecting distal emboli released by such a proximally located device, and then would be removed with the EPAC 10 from the body. An alternate embodiment of the invention is shown in FIG. 7 which shows a metal tip 51 with an abrasive surface on its most forward surface. If the sheathing catheter 40 is then rotated while being advanced through the plaque P, then the ground off plaque can be collected by the plaque collection chamber 17 even if (and preferably so) no other part of EPAC system is rotated.

Various other modifications, adaptations, and alternative designs are of course, possible in light of the above teachings. Therefore, it should be understood that within the scope of the appended claims, the invention may be practiced otherwise than as specifically described herein.

What is claimed is:

1. An apparatus for deployment within a vessel of a living body for removing obstructing tissue on the inner wall of said vessel, the apparatus comprising:

catheter means having a distal portion with a first more proximal region for cutting said obstructing tissue, and a second most distal region for collecting said obstructing tissue after it has been cut from the vessel wall, and said distal portion being capable of assuming a first and a second diameter, said second diameter being larger than said first diameter;

cutting means located at said first more proximal region of said distal portion of the catheter means for cutting said obstructing tissue as the catheter means is pulled back in a retrograde direction through said obstruction tissue;

tissue collecting means having a proximal and a distal end located at said second most distal region of said distal portion of the catheter means for collecting said obstructing tissue as it is cut from the vessel wall;

deployment means for selectively causing said distal portion to assume said first or second diameter; and centering means on aid distal portion of the catheter means for engaging the inner wall of the vessel when said distal portion assumes said second diameter and for preventing the cutting means from contacting and cutting the inner wall of said vessel.

2. The apparatus of claim 1 wherein said collection means is a collection chamber formed of a flexible, deformable plastic.

3. The apparatus of claim 2 wherein said collection chamber is porous for allowing small particulate matter and blood plasma and cells to flow therethrough.

4. The apparatus of claim 2 wherein said collection chamber is treated with heparin.

5. The apparatus of claim 1 wherein said collection means is slidably connected to said cutting means so that rotation of said cutting means does not cause rotation of said collection means.

6. The apparatus of claim 1 wherein said cutting means comprises a radially expandable conical cutter having a multiplicity of radial cutting spokes.

7. The apparatus of claim 6 wherein said radial cutting spokes are curved.

8. The apparatus of claim 1 wherein said deployment means comprises a sheathing catheter having a diameter slightly larger than said first diameter of said distal portion of the catheter means so that when the sheathing catheter surrounds said distal portion, said distal portion assumes said first diameter, and when the sheathing catheter does not surround said distal portion, said distal portion assumes said second diameter.

9. The apparatus of claim 1 wherein said tissue collecting means is positioned at the distal end of said distal portion of the catheter means and said cutting means is positioned at the proximal end of said distal portion of the catheter means.

10. The apparatus of claim 1 wherein the distal end of said tissue collecting means has a diameter smaller than the proximal end of said tissue collecting means.

11. The apparatus of claim 1 wherein said tissue collecting means is conical in shape.

12. The apparatus of claim 1 wherein said deployment means surrounds and compresses said distal portion of the catheter means for causing said distal portion to assume said first diameter.

13. The apparatus of claim 12 wherein said deployment means is a sheathing catheter.

14. The apparatus of claim 12 wherein said deployment means is a guiding catheter.

15. The apparatus of claim 1 wherein said centering means comprises a shoulder having a diameter larger than the diameter of said cutting means and forming the outside of the proximal end of said tissue collecting means so that when said distal portion of the catheter means assumes said second diameter, the shoulder causes the walls of the tissue collecting means to engage the inner wall of the vessel to prevent said cutting means from cutting the wall of the vessel.

16. The apparatus of claim 15 wherein said shoulder is deformable to follow the deformation of the tissue collecting means when the distal portion of said catheter means assumes said first and second diameters.

17. The apparatus of claim 1 wherein said catheter means is coated with a lubricant for facilitating insertion into a vessel.

18. The apparatus of claim 1 and further comprising means for rotating said cutting means while said catheter means is pulled back through said obstructing tissue.

19. The apparatus of claim 1 wherein said cutting means is mechanically vibrated while said catheter means is pulled back through said obstructing tissue.

20. The apparatus of claim 1 wherein said cutting means is connected to an electrical current to perform electrocautery while said catheter means is pulled back through said obstructing tissue.

21. A method for removing obstructing tissue from a vessel within a living body using a catheter system having a distal portion comprising a cutting means and a tissue collection means, said distal portion being capable of assuming a first and second diameter, said first diameter being smaller than said second diameter, said method comprising the steps of:

advancing said catheter system with said distal portion in said first diameter position, through said vessel until the distal portion is just beyond the obstructing tissue;

causing said distal portion of the catheter means to assume said second diameter;

pulling said catheter system back in a retrograde direction through said obstructing tissue to place said cutting means in contact with the obstructing tissue and said cutting means to be of sufficient hardness to form a sharp cutting edge to cut said obstructing tissue away from the wall of the vessel while the cut tissue is collected in the collection means; and withdrawing said catheter system from the vessel along with the cut and collected obstructing tissue.

22. The method of claim 21 wherein said catheter system is advanced through the vessel over a guidewire.

23. The method of claim 21 wherein said catheter system is advanced through the vessel within a guiding catheter.

24. The method of claim 21 wherein said distal portion of the catheter system is caused to assume said first diameter before it is withdrawn from the vessel.

25. The method of claim 21 wherein said vessel is an artery.

26. The method of claim 21 wherein said vessel is a bypass vein.

27. The method of claim 21 wherein said vessel is an artificial graft.

28. The method of claim 21 wherein said obstructing tissue is plaque.

29. The method of claim 21 wherein said obstructing tissue is thrombus.

30. The method of claim 21 wherein said obstructing tissue is both plaque and thrombus.

31. The method of claim 21 wherein said vessel is a ureter.

32. The method of claim 21 wherein said vessel is a urethra.

33. The method of claim 21 wherein said vessel is a tube in the reproductive system.

34. The method of claim 21 wherein said vessel is a tube in the digestive tract.

35. An apparatus for deployment within a vessel of a living body for removing obstructing tissue from said vessel, the apparatus comprising:
  catheter means having a distal portion capable of assuming a first and a second diameter, said second diameter being larger than said first diameter;
  tissue cutting means located proximally to said distal portion of said catheter means, said cutting means being of sufficient hardness to form a sharp cutting edge or grinding surface to cut said obstructing tissue away from the vessel wall;
  tissue collecting means located at said distal portion of said catheter means and being capable of assuming said first of second diameter and being located distally relative to said tissue cutting means, said tissue collecting means being capable of collecting said obstructing tissue after it has been cut from the vessel wall;
  deployment means for selectively causing said distal portion to assume said first or second diameter 36. The apparatus of claim 35 wherein said cutting means is mounted on a separate second catheter in such a manner as to be concentric with said catheter means.

37. A method for removing obstructing tissue from a vessel within a living body using a catheter system having a distal portion comprising a tissue collection means, said distal portion being capable of assuming a first and second diameter, said first diameter being smaller than said second diameter, said method comprising the steps of:
  advancing said catheter system with said distal portion in said first diameter position through said vessel until the distal portion is just beyond the obstructing tissue;
  causing said distal portion of the catheter system to assume said second diameter;
  placing a cutting means of sufficient hardness to form a sharp cutting edge or grinding surface in contact with the obstructing tissue and cutting said obstructing tissue away from the wall of the vessel;
  collecting the cut tissue in said tissue collection means; and
  withdrawing said catheter system from the vessel along with the cut and collected obstructing tissue.

38. The method of claim 37 wherein said cutting means is mounted on a separate second catheter.

* * * * *

REEXAMINATION CERTIFICATE (2387th)
United States Patent [19]
Blythin et al.

[11] B1 4,886,061
[45] Certificate Issued Sep. 13, 1994

[54] ARYL-SUBSTITUTED NAPHTHYRIDINE AND PYRIDOPYRAZINE DERIVATIVES

[75] Inventors: David J. Blythin, North Caldwell; Ho-Jane Shue, Pine Brook, both of N.J.

[73] Assignee: Schering Corporation, Kenilworth, N.J.

Reexamination Request:
No. 90/003,221, Oct. 15, 1993

Reexamination Certificate for:
Patent No.: 4,886,061
Issued: Sep. 12, 1989
Appl. No.: 193,330
Filed: May 12, 1988

Certificate of Correction issued Aug. 20, 1991.

Related U.S. Application Data

[60] Division of Ser. No. 946,118, Dec. 23, 1986, Pat. No. 4,760,073, which is a continuation-in-part of Ser. No. 851,068, Apr. 11, 1986, abandoned.

[51] Int. Cl.$^5$ ............... A61K 31/38; A61K 31/395; C07D 253/06; C07D 471/04
[52] U.S. Cl. ............................... 514/250; 514/242; 514/253; 514/254; 514/256; 514/269; 514/272; 514/273; 514/274; 514/275; 514/292; 514/293; 544/182; 544/238; 544/300; 544/310; 544/316; 544/317; 544/319; 544/320; 544/321; 544/324; 544/328; 544/331; 544/345; 544/333; 544/405; 546/81; 546/82; 546/83; 546/84

[58] Field of Search ............... 514/242, 250, 251, 253, 514/254, 256, 269, 272, 273, 274, 275, 292, 293; 544/182, 238, 300, 310, 316, 317, 319, 320, 321, 324, 328, 331, 333, 345, 405; 546/81, 82, 83, 84

[56] References Cited

U.S. PATENT DOCUMENTS

| | | | |
|---|---|---|---|
| 4,113,731 | 9/1978 | Winters et al. | 514/300 |
| 4,232,017 | 11/1980 | Winters et al. | 514/300 |
| 4,452,800 | 6/1984 | Sherlock | 514/300 |
| 4,492,702 | 1/1985 | Sherlock | 514/300 |
| 4,596,809 | 6/1986 | Sherlock | 514/300 |
| 4,628,055 | 12/1986 | Sherlock | 514/300 |

FOREIGN PATENT DOCUMENTS

| | | | |
|---|---|---|---|
| 0127135 | 12/1984 | European Pat. Off. | 514/300 |
| 4961198 | 11/1989 | Japan | 514/292 |
| 2142013 | 1/1985 | United Kingdom | 514/300 |

OTHER PUBLICATIONS

Kaneko, Eh et al, Chem. Pharm. Bull., 17(6), 1290–1294 (1969).
Fournier et al, La Societe Chemique de France, pp. 364–369 (1968).
Abstract 83–779956 for Japanese 58–144391.
Abstract 101:38382t (Chemical Abstracts, vol. 101 (1984).

*Primary Examiner*—Floyd D. Higel

[57] ABSTRACT

Aryl-substituted naphthyridines and pyridopyrazines are disclosed which are useful in treating allergic reactions, inflammation, peptic ulcers and/or hyperproliferative skin disease. Pharmaceutical compositions and methods of treatment employing such compounds are also disclosed.

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

The patentability of claims 3 to 8 is confirmed.

Claims 1, 2 and 9 are cancelled.

* * * * *